(12) United States Patent
Navon et al.

(10) Patent No.: US 10,957,424 B1
(45) Date of Patent: Mar. 23, 2021

(54) NEURAL NETWORK METHOD OF GENERATING FOOD FORMULAS

(71) Applicant: NotCo Delaware, LLC, Santiago (CL)

(72) Inventors: Yoav Navon, Santiago (CL); Karim Pichara, Santiago (CL); Aadit Patel, Santiago (CL); Ofer Philip Korsunsky, Santiago (CL); Richard Hausman, Santiago (CL)

(73) Assignee: NOTCO DELAWARE, LLC, Santiago (CL)

( * ) Notice: Subject to any disclaimer, the term of this patent is extended or adjusted under 35 U.S.C. 154(b) by 0 days.

(21) Appl. No.: 16/989,413

(22) Filed: Aug. 10, 2020

(51) Int. Cl.
*G16C 20/30* (2019.01)
*G16C 20/10* (2019.01)
*G06K 9/62* (2006.01)
*G06N 3/08* (2006.01)
*G16C 20/70* (2019.01)

(52) U.S. Cl.
CPC ........... *G16C 20/30* (2019.02); *G06K 9/6201* (2013.01); *G06K 9/6289* (2013.01); *G06N 3/084* (2013.01); *G16C 20/10* (2019.02); *G16C 20/70* (2019.02)

(58) Field of Classification Search
CPC .... G06N 3/0445; G06N 3/0454; G06N 3/084; G06N 3/088; G16C 20/10; G16C 20/30; G16C 20/70; G06K 9/6201; G06K 9/6289
See application file for complete search history.

(56) References Cited

U.S. PATENT DOCUMENTS

| | | | |
|---|---|---|---|
| 2017/0116517 A1* | 4/2017 | Chee | G05B 15/02 |
| 2017/0139902 A1* | 5/2017 | Byron | G06Q 10/087 |
| 2018/0192680 A1 | 7/2018 | Fraser | |
| 2019/0171707 A1* | 6/2019 | Rapaport | G06N 3/08 |
| 2019/0228855 A1* | 7/2019 | Leifer | G06N 3/0454 |
| 2019/0228856 A1* | 7/2019 | Leifer | G16H 20/60 |
| 2019/0295440 A1* | 9/2019 | Hadad | G06F 40/216 |
| 2020/0365053 A1 | 11/2020 | Pichara | |

FOREIGN PATENT DOCUMENTS

WO   WO2020/237214   11/2020

OTHER PUBLICATIONS

Hattab et al., Application of an Inverse Neural Network Model for the Identification of Optimal Amendment to Reduce Copper Toxicity in Phytoremediated Contaminated Soils, Journal of Geochemical Exploration, Elsevier, 2014, 136, pp. 14-23, 2014. (Year: 2014).*

(Continued)

*Primary Examiner* — Kamran Afshar
*Assistant Examiner* — Marshall L Werner
(74) *Attorney, Agent, or Firm* — Hickman Becker Bingham Ledesma LLP

(57) ABSTRACT

Techniques to mimic a target food item using artificial intelligence are disclosed. A formula generator is trained using combinations of ingredients. A training set may include, for each combination of ingredients, proportions, and features of the ingredients in a respective combination of ingredients. Given a target food item, the formula generator determines a predicted formula that matches the given target food item. The predicted formula includes a set ingredients and a respective proportion of each ingredient in the set of ingredient.

20 Claims, 5 Drawing Sheets

(56) References Cited

OTHER PUBLICATIONS

The International Searching Authority, "Search Report" in application No. PCT/US2020/034385, dated Jul. 20, 2020, 7 pages.
Current Claims in application No. PCT/US2020/034385, dated Jul. 2020, 5 pages.
Pichara, U.S. Appl. No. 16/416,095, filed May 17, 2019, Office Action, dated Jul. 29, 2019.
Pichara, U.S. Appl. No. 16/416,095, filed May 17, 2019, Final Office Action, dated Dec. 16, 2019.
Pichara, U.S. Appl. No. 16/406,095, filed May 17, 2019, Office Action, dated Nov. 4, 2020.
Patel, U.S. Appl. No. 16/924,006, filed Jul. 8, 2020, Office Action, dated Sep. 9, 2020.
The International Searching Authority, "Search Report" in application No. PCT/US2020/043330, dated Sep. 18, 2020, 16 pages.
Rudinger et al., Skip-Prop: Representing Sentences with One Vector Pre Proposition, 12th International Conference on Computational Semantics, dated 2017, 7 pages.
Kramanolakis et al., "Item Recommendation with Variational Autoencoders and Heterogeneous Priors", DLRS, dated Oct. 2018, 5 pages.
Current Claims in application No. PCT/US2020/043330, dated Sep. 2020, 5 pages.
Bowman et al., "Generating Sentences from a Continuous Space", dated May 2016, 12 pages.
Hui Zou et al., "Regularization and Variable Selection Via the Elastic Net", Department of Statistics, Stanford University, dated Dec. 5, 2003, 29 pages.
Patel, U.S. Appl. No. 16/924,006, filed Jul. 8, 2020, Notice of Allowance, dated Dec. 2, 2020.

* cited by examiner

US 10,957,424 B1

NEURAL NETWORK METHOD OF GENERATING FOOD FORMULAS

TECHNICAL FIELD

One technical field of the present disclosure is artificial intelligence and machine learning, as applied to food. Another technical field is food science. The disclosure relates, in particular, to use of machine learning to generate food formulas for foods that mimic target food items.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Today, many negative consequences of use of animals in the food industry are known, such as deforestation, pollution, human health conditions, and allergies, among others. In contrast, a plant-based diet is associated with improved health and well-being and reduces risk of diseases. Not only is a plant-based diet good for our health but it is also good for the Earth's health. Research has shown that production of plant-based food items generates less greenhouse emissions and require less energy, water, and land than production of animal-based food items. There are plant alternatives to animal-based food items. For example, plant alternatives to meat include veggie burgers and other vegan meat food items. However, these alternatives do not match the taste and texture of meat.

Accordingly, there is a need for improved techniques to mimic a target food item, such as an animal-based target food item, by matching nutritional and sensory attributes as much as possible. Unfortunately, many techniques for development of new foods rely upon time-consuming, inaccurate, manual laboratory work in which different ingredients are combined in different ways and tested. These approaches are inefficient, involve extensive time to develop a single successful food formula, and waste physical resources.

SUMMARY

The appended claims may serve as a summary of the invention.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

Figure 1:
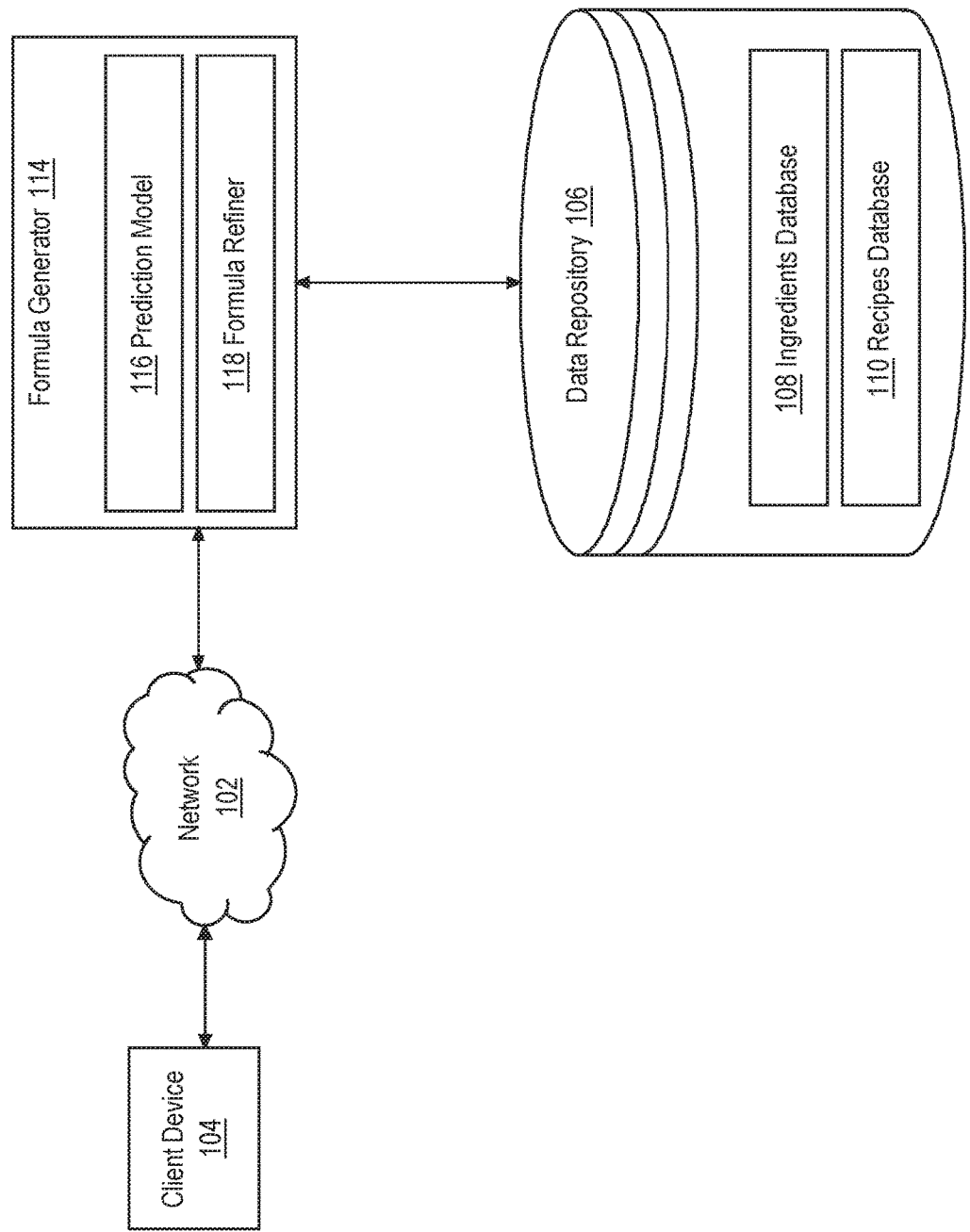
FIG. 1 illustrates an example networked computer system with which various embodiments may be practiced.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

Embodiments are described herein in sections according to the following outline:

1.0 GENERAL OVERVIEW
2.0 STRUCTURAL OVERVIEW
3.0 FUNCTIONAL OVERVIEW
3.1 PREDICTION MODEL
3.2 FORMULA REFINER
4.0 PROCEDURAL OVERVIEW
5.0 HARDWARE OVERVIEW
6.0 SOFTWARE OVERVIEW
7.0 OTHER ASPECTS OF DISCLOSURE 1.0 General Overview A set of computer programs implements a formula generator that includes a neural network. During a training stage, selected parameters of the neural network are modified by matching sets of ingredients and corresponding sets of features. Examples of the parameters may include parameters weight values or bias threshold values. During a prediction stage, the trained neural network may be applied to a set of features of a target food item to generate a predicted formula that mimics the target food item In an embodiment, a computer-implemented method to generate a predicted formula of a plant-based food item to mimic a target food item that is not plant-based, comprises collecting first digital data representing combinations of ingredients and determining features of each combination of the combinations of ingredients. The method also includes generating a plurality of digitally stored feature vectors, comprising representing the features of each combination of the combinations of ingredients as a digitally stored feature vector. The method also includes generating a plurality of digitally stored ingredients vectors, comprising representing each combination of the combinations of ingredients as a digitally stored ingredients vector. The method also includes creating a training set for use in training a neural network. The training set comprises the plurality of digitally stored feature vectors and the plurality of digitally stored ingredients vectors associated with the combinations of ingredients. The method also includes training, using the training set, the neural network in a first stage to match the plurality of digitally stored feature vectors and the plurality of digitally stored ingredients vectors by modifying parameters of the neural network. The method also includes identifying features of the target food item and, in response, representing the features of the target food item as a digitally stored feature vector, and applying the trained neural network to the digitally stored feature vector of the target food item in a second stage to generate a predicted formula that includes a set of ingredients and a respective proportion of each ingredient in the set of ingredients.

Other embodiments, aspects, and features will become apparent from the reminder remainder of the disclosure as a whole.

2.0 Structural Overview

FIG. 1 illustrates an example networked computer system 100 with which various embodiments may be practiced. FIG. 1 is shown in simplified, schematic format for purposes of illustrating a clear example and other embodiments may include more, fewer, or different elements. FIG. 1, and the other figures and all of the description and claims in this disclosure, are intended to present, disclose and claim a technical system and technical methods comprising specially programmed computers, using a special-purpose distributed computer system design and instructions that are programmed to execute the functions that are described. These elements execute functions that have not been available before to provide a practical application of computing technology to the problem of generating formulas for plant-based foods. In this manner, the disclosure presents a technical solution to a technical problem, and any interpretation of the disclosure or claims to cover any judicial exception to patent eligibility, such as an abstract idea, mental process, method of organizing human activity or mathematical algorithm, has no support in this disclosure and is erroneous.

In some embodiments, the networked computer system comprises one or more client devices represented by client device 104, a server computer, and one or more data repositories represented by data repository 106, which are communicatively coupled directly or indirectly via one or more networks 102.

The server computer utilizes a set of one or more computer programs or sequences of program instructions that implement machine learning algorithms to generate a formula using ingredients to mimic a given target food item in flavor, color, feel and/or functionality. Programs or sequences of instructions organized to implement the formula generating functions in this manner may be referred to herein as a formula generator. In an embodiment, the server computer broadly represents one or more computers, such as one or more desktop computers, server computers, a server farm, a cloud computing platform, or a parallel computer, virtual computing instances in public or private datacenters, and/or instances of a server-based application. Cloud computing implementations may use Amazon EC2, Google Cloud, or container orchestration via Kubernetes or Docker.

The formula generator 114 comprises a prediction model 116 and a formula refiner 118. The components of the formula generator 114 may be implemented using software, hardware, firmware, or a combination thereof. In one embodiment, each of the prediction model 116 and the formula refiner 118 comprises one or more sequences of computer program instructions that are programmed to execute the functions that are described herein for the foregoing elements. In an embodiment, one or more components of the formula generator 114 may include a processor configured to execute instructions stored in a non-transitory computer readable medium.

In an embodiment, the prediction model 116 is programmed to learn relationships between input data and output data. The input data and output data may include target features (e.g., chemical, nutritional, and/or molecular features) and formulas (e.g., ingredients and respective proportions). For example, the input data may be target features and the output data may be formulas. Alternatively, the input data may be formulas and the output data may be target features.

The prediction model 116 may include a neural network that uses a training set of target features and formulas to update a set of weights to best map the input data to the output data. The training process may be solved using an optimization algorithm that searches through a space of possible values for the set of weights that results in good performance on the training set. Once the neural network is trained, the neural network may generate or predict a formula (e.g., a set of ingredients and corresponding proportions), based on a target food item, that mimics the target food item.

In an embodiment, the formula refiner 118 is programmed to reduce the number of ingredients in a predicted formula such that the predicted formula includes only the top K (e.g., 20) ingredients. The formula refiner 118 is also programmed to update or rebalance respective proportions of the remaining ingredients in the predicted formula.

In some embodiments, in keeping with sound software engineering principles of modularity and separation of function, the prediction model 116 and the formula refiner 118 are implemented as a logically separate program, process or library.

Computer executable instructions described herein may be in machine executable code in the instruction set of a CPU and may have been compiled based upon source code written in Python, JAVA, C, C++, OBJECTIVE-C, or any other human-readable programming language or environment, alone or in combination with scripts in JAVASCRIPT, other scripting languages and other programming source text. In another embodiment, the programmed instructions also may represent one or more files or projects of source code that are digitally stored in a mass storage device such as non-volatile RAM or disk storage, in the systems of FIG. 1 or a separate repository system, which when compiled or interpreted cause generating executable instructions which when executed cause the computer to perform the functions or operations that are described herein with reference to those instructions. In other words, the drawing figure may represent the manner in which programmers or software developers organize and arrange source code for later compilation into an executable, or interpretation into bytecode or the equivalent, for execution by the formula generator 114.

The formula generator 114 may be coupled to the data repository 106 that includes an ingredients database 108 and a recipes database 110.

The ingredients database 108 includes raw ingredients from various sources, such as from USDA's National Agricultural Library. An ingredient may be plant-based, animal-based, water-based, synthetic, or a combination thereof. Some non-limiting examples of plant-based ingredients may include vegetables (e.g., onions, potatoes, garlic, spinach, carrots, celery, squash, etc.), fruits (e.g., apples, pears, grapes, etc.), herbs (e.g., oregano, cilantro, basil, etc.), spices (e.g., black peppers, turmeric, red chili peppers, cinnamon, etc.), oils (e.g., corn oil, olive oil, etc.), nuts (e.g., almonds, walnuts, pistachios, etc.), legumes (e.g., lentils, dried peas, soybeans, etc.), starch, proteins, fibers, carbohydrates, sugar, etc. Some non-limiting examples of animal-based ingredients may include dairy products (e.g., milk, butter, cheese, yogurt, ice cream, etc.), egg-based products (e.g., mayonnaise, salad dressings, etc.), meat products (e.g., burger patties, sausages, hot dogs, bacon, etc.), and/or seafood (e.g., fish, crab, lobsters, etc.). Synthetic ingredients may include artificially produced food, e.g., artificial meats, artificial sweeteners, artificial milk, etc.

In an embodiment, each ingredient in the ingredients database 108 may be associated with a feature vector, which is a list of values relating to chemical, nutritional, and/or molecular features or descriptors. Feature vectors may be stored with the ingredients in the ingredients database 108 or separately from the ingredients in another database.

The recipes database 110 includes recipes collected by scraping various websites and proprietary recipes. Each recipe may include raw text. As an example, each recipe may include a list of ingredients that may specify a name of each ingredient, quantity or amount of each ingredient, a state of each ingredient (e.g., four avocadoes, halved and pitted). Each recipe may also include directions to describe a list of instructions for cooking the ingredients. In an embodiment, a recipe may also include properties of the food dish associated with the recipe. The properties may include human sensorial feedback such as taste (e.g., salt, sweet, bitter, sour, and umami), texture descriptors, acceptance, and the like, and a picture of the food dish. In an embodiment, color(s) may be extracted from the picture and associated with the recipe.

In an embodiment, the proprietary recipes may be plant-based and include human feedback. In an embodiment, the proprietary recipes are developed by the Applicant. In an embodiment, the proprietary recipes may be stored in a different database separate from other recipes, such as those collected by scraping various website.

In an embodiment, each recipe in the recipes database 110 may be associated with an ingredients vector, which is a list of values relating to proportions of ingredients in a respective recipe. The proportions of ingredients may be based on the quantity or amount of each ingredient specified in the recipe. Ingredients vectors may be stored with the recipes in the recipes database 110 or separately from the recipes in another database.

Each database 108, 110 may be implemented using memory, e.g., RAM, EEPROM, flash memory, hard disk drives, optical disc drives, solid state memory, or any type of memory suitable for database storage.

The network 102 broadly represents a combination of one or more local area networks (LANs), wide area networks (WANs), metropolitan area networks (MANs), global interconnected internetworks, such as the public internet, or a combination thereof. Each such network may use or execute stored programs that implement internetworking protocols according to standards such as the Open Systems Interconnect (OSI) multi-layer networking model, including but not limited to Transmission Control Protocol (TCP) or User Datagram Protocol (UDP), Internet Protocol (IP), Hypertext Transfer Protocol (HTTP), and so forth. All computers described herein may be configured to connect to the network 102 and the disclosure presumes that all elements of FIG. 1 are communicatively coupled via the network 102. The various elements depicted in FIG. 1 may also communicate with each other via direct communications links that are not depicted in FIG. 1 for purposes of explanation.

The formula generator 114 is accessible over the network 102 by multiple computing devices, such as a client device 104, to request a predicted formula (e.g., a set of ingredients and corresponding proportions) based on a target food item. The client device 104 may comprise a desktop computer, laptop computer, tablet computer, smartphone, or any other type of computing device that allows access to the formula generator 114. The elements in FIG. 1 are intended to represent one workable embodiment but are not intended to constrain or limit the number of elements that could be used in other embodiments.

3.0 Functional Overview

In an embodiment, the prediction model 116 and the formula refiner 118 interoperate programmatically in an unconventional manner to generate a predicted formula, for a target food item, with specific and/or desired characteristics. The predicted formula may be a combination of one or more ingredients and a respective proportion (e.g., percentage) of each ingredient in the combination. The predicted formula mimics the target food item. For example, a target food item may be an animal-based target food item (e.g., an animal-based brownie), and ingredients in a predicted formula may be plant-based ingredients.

A predicted formula may be displayed on the client device 104. In an embodiment, the predicted formula may be transmitted downstream to a recipe generator for further processing such as to determine a new recipe including a set of cooking directions or instructions for that formula. An example recipe generator is described in U.S. application Ser. No. 16/416,095, filed May 17, 2019, titled "Systems and Methods to Mimic Target Good Items using Artificial Intelligence," the entire contents of which are hereby incorporated by reference for all purposes as if fully set forth herein.

3.1 Prediction Model

As described above, the prediction model 116 uses a neural network to predict formulas. During a training stage, the neural network uses a learning algorithm, such as gradient descent, to modify parameters (e.g., a set of weights, bias thresholds) of the neural network. The gradient descent may be based on batch gradient descent, stochastic gradient descent, or mini-batch gradient descent. A training set for the neural network may include different datasets, such as a synthetic dataset and a true dataset. Each dataset includes combinations of ingredients. The synthetic dataset may include combinations of randomly selected ingredients (e.g., ingredients from ingredients database 108). The true dataset may include combinations of actual ingredients from recipes (e.g., recipes in the recipes database 110). Each combination of ingredients may be represented differently as two digitally stored vectors, as further discussed below. A combination of ingredients may be represented as a feature vector describing features of the ingredients in the combination of ingredients. A combination of ingredients may also be represented a formula vector describing the ingredients in the combination of ingredients and respective proportions of those ingredients.

Figure 2A:
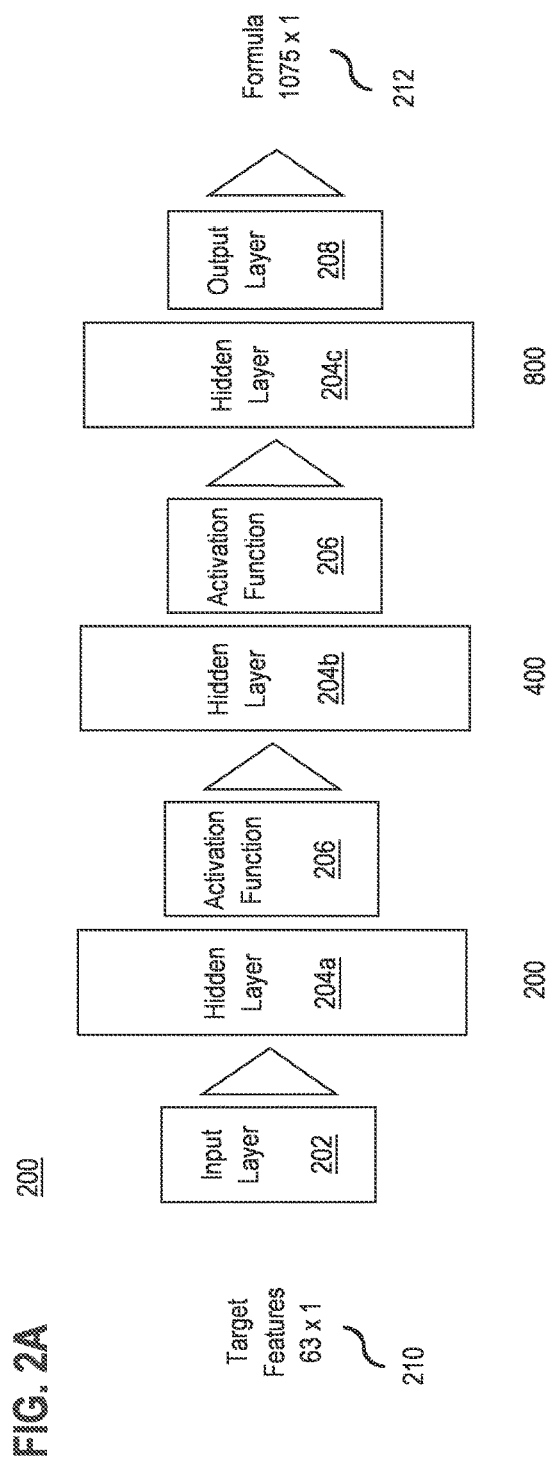
FIG. 2A, FIG. 2B illustrate example prediction models in accordance with some embodiments.

FIG. 2A illustrates an example neural network in accordance with some embodiments.

In an embodiment, a neural network 200 is programmed using PYTORCH, SPARKCOGNITION, DECI.AI, TENSORFLOW, KERAS, or other commercially available neural network SaaS software and a set of configuration values or other input that specify the number of layers, features, and other aspects of the neural network 200. The neural network 200 is referred herein as a direct neural network.

In an embodiment, the neural network 200 is programmed to receive target features, such as a set of features of a target food item, as input data 210 and to predict a formula as output data 212. The input data 210 (e.g., the set of features of the target food item) may be digitally stored in memory as a feature vector. The set of features of the target food item and a respective set of features for each ingredient in the ingredients database 108 may be associated with a same set of feature types. The output data 212 (e.g., the predicted formula) may be digitally stored in memory as an ingredients vector of one or more ingredients and respective proportions of those ingredients. In an embodiment, the input data 210 may have a dimension of 63×1, and the output data 212 may have a dimension of 1075×1. Other embodiments may use different dimensions in a range of [20-500] for the input data 210 and in a range of [1000-10000] for the output data 212.

In an embodiment, the neural network 200 is programmed to have an input layer 202, a plurality of hidden layers 204 (collectively), an activation function 206, and an output layer 208. The input layer 202 of the neural network 200 is programmed to receive and pass the input data 210 to the next layer of the neural network 200 (e.g., hidden layer 204*a*).

The neural network 200 is programmed with three (3) hidden layers 204a, 204b, 204c. The size of each of the hidden layers 204a, 204b, 204c is doubled such that the size of the last hidden layer 204c is similar to the size of the output data 212. For example, the size of the hidden layer 204a is 200, the size of the hidden layer 204b is 400, and the size of the hidden layer 204c is 800. Other embodiments may use a different number of hidden layers and/or different hidden layer dimensions, depending on the dimensions of the input data 210 and the output data 212.

Connections between neurons of the hidden layers 204 of the neural network 200 are weighted. In an embodiment, the network 200 may be programmed so that the weights are initialized using an initialization technique such as Xavier Initialization, He Initialization, Glorot Initialization, or another suitable initialization technique. In an embodiment, the network 200 may be programmed so that the weights are randomly initialized.

The hidden layers 204 are programmed to perform intermediate processing or computation and transfer the weights from one layer to the next layer. Each hidden layer 204 may be programmed to implement a regularization technique to prevent the neural network 200 from overfitting. Example regularization technique is dropout. Each hidden layer may have a configurable dropout rate (e.g., 50%) to reduce interdependent learning among the neurons.

The activation function 206 defines the activation or output of a neuron given the weighted input and improves the neural network 200 by speeding up training. Example activation function 206 may be a rectified linear activation unit (ReLU). Another activation function, such as a sigmoid activation function, a tan h activation function, or a leaky ReLU may be used. The hidden layers 204 may be programmed to use different activation functions 206.

The output layer 208 uses a softmax function that maps the output of the hidden layers 204 immediately preceding it to the output data 212 of the entire neural network 200.

Table 1 includes example code describing the direct neural network 200.

TABLE 1

```
dropout = 0.5
num_ingredients = 1700
food_features = 64
input_target = Input(shape=(food_features,))
f = Dense(64, activation="relu")(input_target)
f = Dropout(dropout) (f, training=True)
f = Dense(200, activation="relu") (f)
f = Dropout(dropout) (f, training=True)
f = Dense(400, activation="relu") (f)
f = Dropout(dropout) (f, training=True)
f = Dense(800, activation="relu") (f)
f = Dropout(dropout) (f, training=True)
y_pred = Dense(num_ingredients, activation="softmax",
name ="y_pred") (f)
model = Model(inputs=input_target, outputs=y_pred)
```

In an embodiment, the learning algorithm of the neural network 200 may be programmed as a supervised learning algorithm. The training data includes linear combinations of ingredients. A linear combination of ingredients in the training data for the neural network 200 may be represented as a vector of features of all ingredients in a combination of ingredients. The combination of ingredients may be a synthetic combination of ingredients (e.g., a combination of ingredients randomly selected from the ingredients in the ingredients database 108) or a true combination of ingredients (e.g., a combination of actual ingredients in a recipe from the recipes in the recipes database 110). Each feature vector, as an input during training, is associated with a known target. The known target may be an ingredients vector associated with the combination of ingredients. The neural network 200 is trained by readjusting the set of weights and bias thresholds such that the output of the neural network 200, given the input, matches the known target. Cross-entropy or mean squared error may be used as a loss function of the neural network 200.

During the prediction phase, the neural network 200 is applied to a target food item. The neural network 200 receives features of the target food item as the input data 210. The features of the target food item may be digitally stored in memory as a feature vector. The neural network 200 generates a predicted formula as the output data 212. The predicted formula may be represented as an ingredients vector describing one or more ingredients and respective proportions of those ingredients.

Figure 2B:
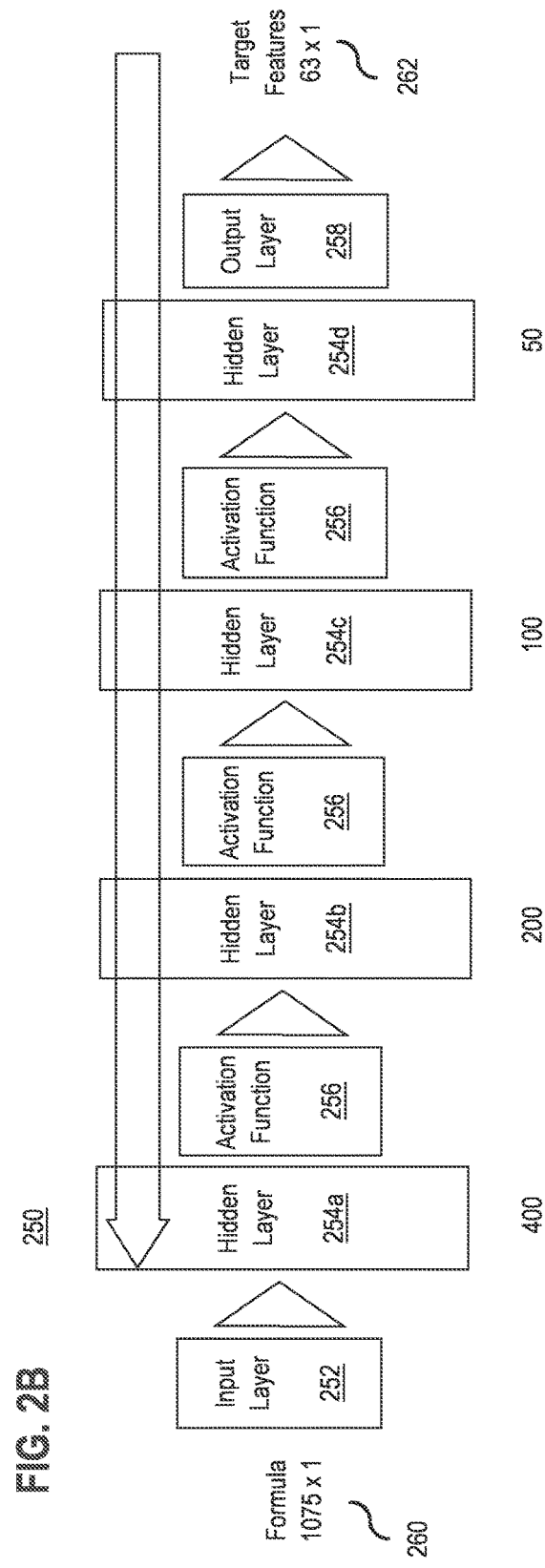

FIG. 2B illustrates another example neural network in accordance with some embodiments.

In an embodiment, neural network 250 is programmed using PYTORCH, SPARKCOGNITION, DECI.AI, TENSORFLOW, KERAS, or other commercially available neural network SaaS software and a set of configuration values or other input that specify the number of layers, features, and other aspects of the neural network 250. The neural network 250 is referred herein as an inverse neural network.

In an embodiment, the neural network 250 is programmed to predict input data 260 (e.g., a formula), given output data 262 (e.g., a set of features of a target food item), by running the neural network 250 backwards or in reverse, as further described below. The output data 252 (e.g., the set of features of the target food item) may be digitally stored in memory as a feature vector. The set of features of the target food item and a respective set of features for each ingredient in the ingredients database 108 may be associated with a same set of feature types. The input data 260 (e.g., the predicted formula) may be digitally stored in memory as an ingredients vector of one or more ingredients and respective proportions of those ingredients. In an embodiment, the input data 260 may have a dimension of 1075×1, and the output data 262 may have a dimension of 63×1. Other embodiments may use different dimensions in a range of [20-500] for the input data 260 and in a range of [1000-10000] for the output data 262.

In an embodiment, the neural network 250 is programmed to have an input layer 252, a plurality of hidden layers 254 (collectively), an activation function 256, and an output layer 258. The input layer 252 of the neural network 250 is programmed to receive and pass the input data 260 to the next layer of the neural network 250 (e.g., hidden layer 254a).

The neural network 250 is programmed with four (4) hidden layers 254a, 254b, 254c, 254d. The size of each of the hidden layers 254a, 254b, 254c, 254d is halved such that the size of the last hidden layer 254d is similar to the size of the output data 262. For example, the size of the hidden layer 254a is 400, the size of the hidden layer 254b is 200, the size of the hidden layer 254c is 100, and the size of the hidden layer 254d is 50. Other embodiments may use a different number of hidden layers and/or different hidden layer dimensions, depending on the dimensions of the input data 260 and the output data 262.

Connections between neurons of the hidden layers 254 of the neural network 250 are weighted. In an embodiment, the network 250 may be programmed so that the weights are initialized using an initialization technique such as Xavier Initialization, He Initialization, Glorot Initialization, or another suitable initialization technique. In an embodiment, the network 250 may be programmed so that the weights are randomly initialized. The hidden layers 254 are programmed to perform intermediate processing or computation and transfer weights from one layer to the next layer.

The activation function 256 defines the activation or output of a neuron given the weighted input and improves the neural network 250 by speeding up training. Example activation function 256 may be a rectified linear activation unit (ReLU). Another activation function, such as a sigmoid activation function, a tan h activation function, or a leaky ReLU may be used. The hidden layers 254 may be programmed to use different activation functions.

The output layer 258 uses a softmax function that maps the output of the hidden layers 254 immediately preceding it to the output data 252 of the entire neural network 250.

Table 2 includes example code describing the inverse neural network 250.

TABLE 2

```
num_ingredients = 1700
food_features = 64
model = Sequential( )
model.add(Dense(400, input_dim=num_ingredients, activation="relu"))
model.add(Dense(200, activation="relu"))
model.add(Dense(100, activation="relu"))
model.add(Dense(50, activation="relu"))
model.add(Dense(food_features, activation ="sigmoid"))
```

In an embodiment, the learning algorithm of the neural network 250 may be programmed as a supervised learning algorithm. The training data includes linear combinations of ingredients. A linear combination of ingredients in the training data of the neural network 250 may be represented as a vector of all ingredients in a combination of ingredients and respective proportions of those ingredients. The combination of ingredients may be a synthetic combination of ingredients (e.g., a combination of ingredients randomly selected from the ingredients in the ingredients database 108). Respective proportions of the randomly selected ingredients may be randomly assigned as long as the sum of all proportions is one (1). The combination of ingredients may be a true combination of ingredients (e.g., a combination of actual ingredients in a recipe from the recipes in the recipes database 110). Respective proportions of actual ingredients may be determined from quantities or amounts of the ingredients specified in the recipe.

Each ingredients vector, as an input during training, is associated with a known target. The known target may be a feature vector associated with the combination of ingredients. The neural network 250 is trained by readjusting the set of weights and bias thresholds such that the output of the neural network 250, given the input, matches the known target. Cross-entropy or mean squared error may be used as a loss function of the neural network 250.

During the prediction phase, the neural network 250 may be run in reverse or backwards to obtain an input, which would be a predicted formula, such that the predicted formula could have produced an output that matches a desired target. In an embodiment, a process similar to that of gradient descent may be performed, back projecting values through the neural network 250, to reverse the activation function 256 and inverse operations of the hidden layers 254 to obtain the predicted formula. Trace ingredients may be clipped during the gradient descent process to remove those ingredients with almost negligible contribution to obtain a predicted formula that includes significant ingredients. Trace ingredients may be manually clipped or automatically clipped.

3.2 Formula Refiner

The formula refiner 118 is programmed to refine a predicted formula by reducing the number of ingredients in the predicted formula to K ingredients that have the highest proportions and rebalancing the proportions of the remaining K ingredients. For example, the formula refiner 118 may programmed to select the top 20 ingredients that have the greatest proportions.

In an embodiment, the formula refiner 118 may be programmed to rebalance the proportions of the K ingredients in the predicted formula by renormalizing the predicted proportions of the K ingredients in the predicted formula. For example, the formula refiner 118 may be programmed to divide each of the predicted proportions by the sum of all predicted proportions.

In an embodiment, the formula refiner 118 may be programmed to rebalance the proportions by performing Lasso regression over the K ingredients. For example, all predicted proportions of the K ingredients are discarded, and new proportions for the K ingredients are determined to match a target vector.

In an embodiment, an updated predicted formula may be displayed on a client device 104 and/or may be passed as input into a recipe generator to determine cooking directions for the updated predicted formula.

4.0 Procedural Overview

Figure 3:
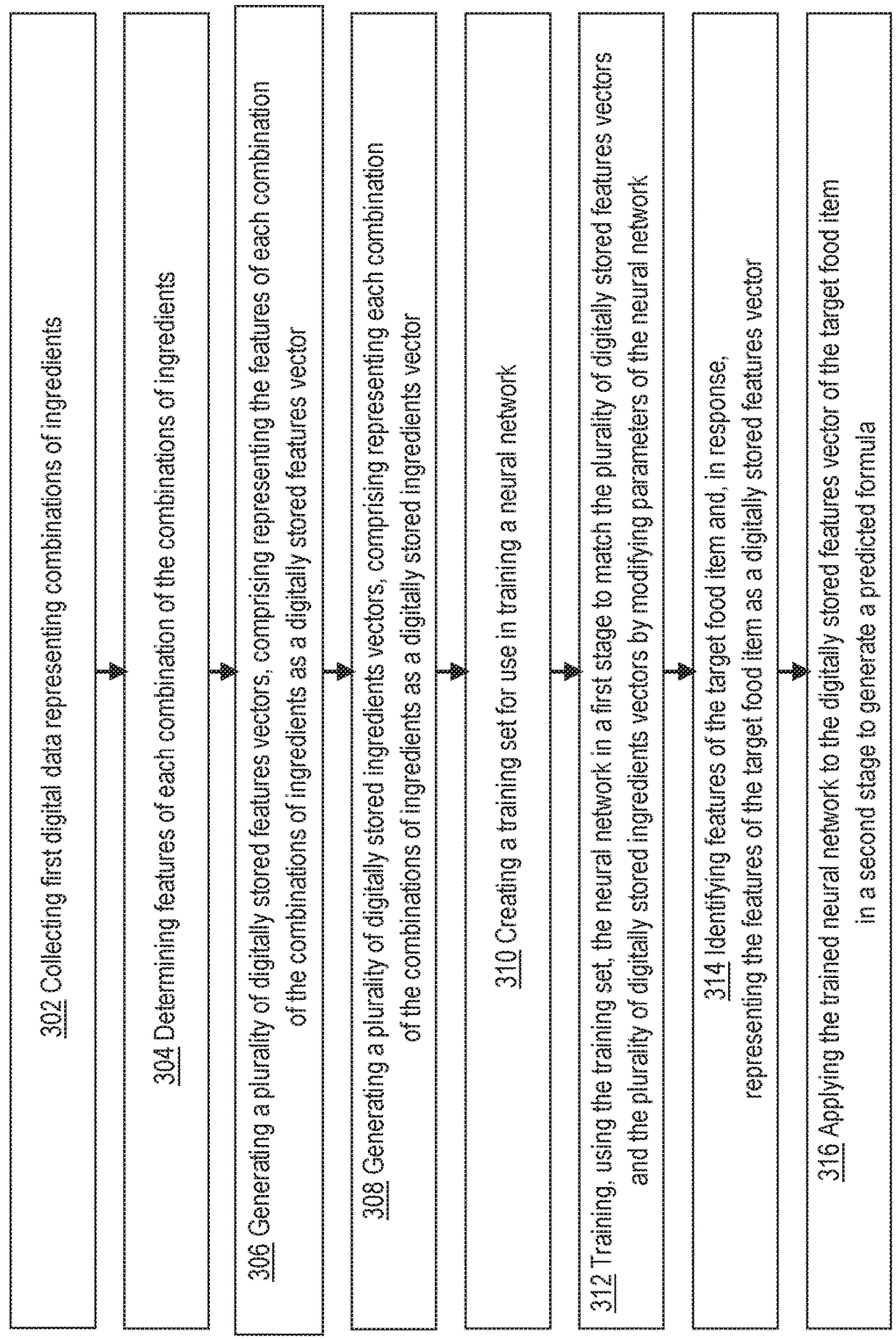
FIG. 3 illustrates an example method to generate a predicted formula in accordance with some embodiments.

FIG. 3 illustrates an example method to generate a predicted formula of a plant-based food item to mimic a target food item that is not plant-based, in accordance with some embodiments. FIG. 3 may be used as a basis to code a method 300 as one or more computer programs or other software elements that a formula generator can execute or host.

At step 302, first digital data representing combinations of ingredients is collected. The combinations of ingredients may include true combinations of ingredients. The true combinations of ingredients may be from recipes in a recipes database. The combinations of ingredients may include synthetic combinations of ingredients. Each synthetic combination of ingredients of the synthetic combinations of ingredients may include ingredients randomly selected from an ingredients database. The random selection may be automated or manual.

At step 304, features of each combination of the combinations of ingredients are determined. The features may relate to chemical, nutritional, and/or molecular features. In an embodiment, features of each ingredient may be stored with a respective ingredient in the ingredients database.

At step 306, a plurality of digitally stored feature vectors is generated. In an embodiment, each combination of the combinations of ingredients is represented as a digitally stored feature vector. Each digitally stored feature vector associated with a combination of ingredients represents a set of features including at least one chemical feature, nutritional feature, and molecular feature of each ingredient in the combination of ingredients.

At step 308, a plurality of digitally stored ingredients vectors is generated. In an embodiment, each combination of the combinations of ingredients is represented as a digitally stored ingredients vector. Each digitally stored ingredients vector associated with a combination of ingredients includes a proportion of each ingredient in the combination of ingredients.

In an embodiment, proportions of randomly selected ingredients of each synthetic combination of ingredients may be randomly assigned. In an embodiment, proportions of actual ingredients of each true combination of ingredients may be determined from quantities and amounts of the ingredients specified in a respective recipe. In an embodiment, the sum of all proportions of the ingredients is one (1).

At step 310, a training set is created for use in training a neural network. The training set comprises the plurality of digitally stored feature vectors and the plurality of digitally stored ingredients vectors associated with the combinations of ingredients.

At step 312, the neural network is trained using the training set, in a first stage, to match the plurality of digitally stored feature vectors and the plurality of digitally stored ingredients vectors by modifying parameters of the neural network.

For example, the first stage is a training stage. In an embodiment, during the training stage, parameters of the neural network are modified such that an output of the neural network, given a digitally stored feature vector of the plurality of digitally stored feature vectors, matches a corresponding digitally stored ingredients vector from the plurality of digitally stored ingredients vectors. In an embodiment, during the training stage, parameters of the neural network are modified such that an output of the neural network, given a digitally stored ingredients vector of the plurality of digitally stored ingredients vectors, matches a corresponding feature vector from the plurality of digitally stored feature vectors.

At step 314, features of the target food item are identified, and, in response, the features of the target food item are represented as a digitally stored feature vector. The digitally stored feature vector associated with the target food item represents a set of features including at least one chemical feature, nutritional feature, and molecular feature.

At step 316, the trained neural network is applied to the digitally stored feature vector of the target food item, in a second stage, to generate a predicted formula that includes a set of ingredients and a respective proportion of each ingredient in the set of ingredients.

For example, the second stage is a prediction stage. In an embodiment, during the prediction stage, the trained neural network may be applied in reverse in the second stage to generate the predicted formula. For example, the neural network may be run in reverse or backwards to obtain an input, which is the predicted formula, such that the predicted formula could have produced an output that matches an output, which is the target features. In an embodiment, during the prediction stage, the trained neural network may be applied directly (e.g., not in reverse) in the second stage to generate the predicted formula. For example, the neural network receives the target features to generate the predicted formula.

In an embodiment, the predicted formula may be refined to reduce a total number of ingredients in the set of ingredients and to rebalance proportions of remaining ingredients in the set of ingredients. For example, the top K ingredients in the set of ingredients that have the greatest or highest proportions are selected, and the other ingredients are dropped from the set of ingredients. In an embodiment, the predicted formula may be used to prepare the plant-based food item.

5.0 HARDWARE OVERVIEW

According to one embodiment, the techniques described herein are implemented by at least one computing device. The techniques may be implemented in whole or in part using a combination of at least one server computer and/or other computing devices that are coupled using a network, such as a packet data network. The computing devices may be hard-wired to perform the techniques or may include digital electronic devices such as at least one application-specific integrated circuit (ASIC) or field programmable gate array (FPGA) that is persistently programmed to perform the techniques or may include at least one general purpose hardware processor programmed to perform the techniques pursuant to program instructions in firmware, memory, other storage, or a combination. Such computing devices may also combine custom hard-wired logic, ASICs, or FPGAs with custom programming to accomplish the described techniques. The computing devices may be server computers, workstations, personal computers, portable computer systems, handheld devices, mobile computing devices, wearable devices, body mounted or implantable devices, smartphones, smart appliances, internetworking devices, autonomous or semi-autonomous devices such as robots or unmanned ground or aerial vehicles, any other electronic device that incorporates hard-wired and/or program logic to implement the described techniques, one or more virtual computing machines or instances in a data center, and/or a network of server computers and/or personal computers.

Figure 4:
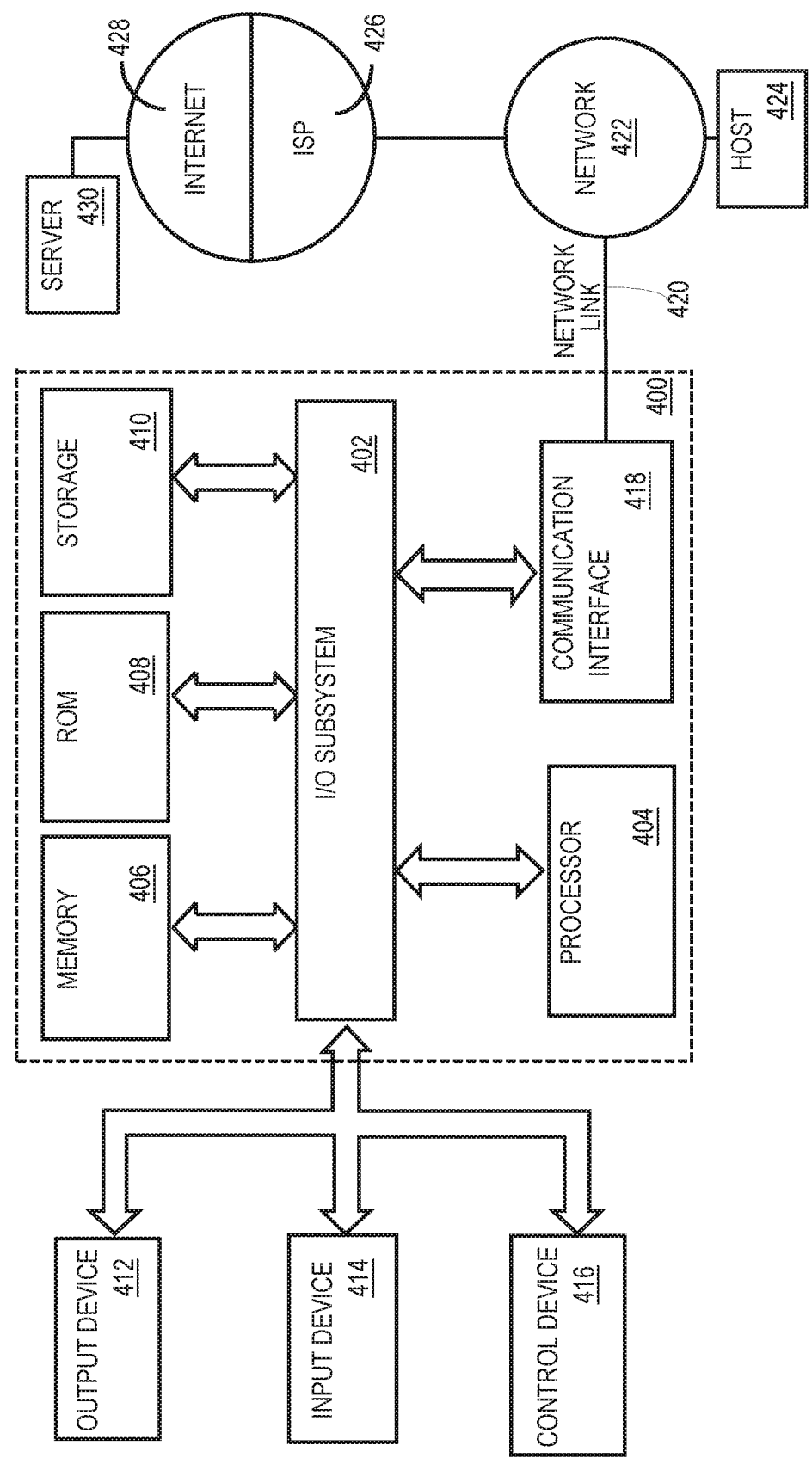
FIG. 4 illustrates a block diagram of a computing device in which the example embodiment(s) of the present invention may be embodiment.

FIG. 4 is a block diagram that illustrates an example computer system with which an embodiment may be implemented. In the example of FIG. 4, a computer system 400 and instructions for implementing the disclosed technologies in hardware, software, or a combination of hardware and software, are represented schematically, for example as boxes and circles, at the same level of detail that is commonly used by persons of ordinary skill in the art to which this disclosure pertains for communicating about computer architecture and computer systems implementations.

Computer system 400 includes an input/output (I/O) subsystem 402 which may include a bus and/or other communication mechanism(s) for communicating information and/or instructions between the components of the computer system 400 over electronic signal paths. The I/O subsystem 402 may include an I/O controller, a memory controller and at least one I/O port. The electronic signal paths are represented schematically in the drawings, for example as lines, unidirectional arrows, or bidirectional arrows.

At least one hardware processor 404 is coupled to I/O subsystem 402 for processing information and instructions. Hardware processor 404 may include, for example, a general-purpose microprocessor or microcontroller and/or a special-purpose microprocessor such as an embedded system or a graphics processing unit (GPU) or a digital signal processor or ARM processor. Processor 404 may comprise an integrated arithmetic logic unit (ALU) or may be coupled to a separate ALU.

Computer system 400 includes one or more units of memory 406, such as a main memory, which is coupled to I/O subsystem 402 for electronically digitally storing data and instructions to be executed by processor 404. Memory 406 may include volatile memory such as various forms of random-access memory (RAM) or other dynamic storage device. Memory 406 also may be used for storing temporary variables or other intermediate information during execution of instructions to be executed by processor 404. Such instructions, when stored in non-transitory computer-readable storage media accessible to processor 404, can render computer system 400 into a special-purpose machine that is customized to perform the operations specified in the instructions.

Computer system 400 further includes non-volatile memory such as read only memory (ROM) 408 or other static storage device coupled to I/O subsystem 402 for storing information and instructions for processor 404. The ROM 408 may include various forms of programmable ROM (PROM) such as erasable PROM (EPROM) or electrically erasable PROM (EEPROM). A unit of persistent storage 410 may include various forms of non-volatile RAM (NVRAM), such as FLASH memory, or solid-state storage, magnetic disk, or optical disk such as CD-ROM or DVD-ROM and may be coupled to I/O subsystem 402 for storing information and instructions. Storage 410 is an example of a non-transitory computer-readable medium that may be used to store instructions and data which when executed by the processor 404 cause performing computer-implemented methods to execute the techniques herein.

The instructions in memory 406, ROM 408 or storage 410 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. The instructions may implement a web server, web application server or web client. The instructions may be organized as a presentation layer, application layer and data storage layer such as a relational database system using structured query language (SQL) or no SQL, an object store, a graph database, a flat file system or other data storage.

Computer system 400 may be coupled via I/O subsystem 402 to at least one output device 412. In one embodiment, output device 412 is a digital computer display. Examples of a display that may be used in various embodiments include a touch screen display or a light-emitting diode (LED) display or a liquid crystal display (LCD) or an e-paper display. Computer system 400 may include other type(s) of output devices 412, alternatively or in addition to a display device. Examples of other output devices 412 include printers, ticket printers, plotters, projectors, sound cards or video cards, speakers, buzzers or piezoelectric devices or other audible devices, lamps or LED or LCD indicators, haptic devices, actuators, or servos.

At least one input device 414 is coupled to I/O subsystem 402 for communicating signals, data, command selections or gestures to processor 404. Examples of input devices 414 include touch screens, microphones, still and video digital cameras, alphanumeric and other keys, keypads, keyboards, graphics tablets, image scanners, joysticks, clocks, switches, buttons, dials, slides, and/or various types of sensors such as force sensors, motion sensors, heat sensors, accelerometers, gyroscopes, and inertial measurement unit (IMU) sensors and/or various types of transceivers such as wireless, such as cellular or Wi-Fi, radio frequency (RF) or infrared (IR) transceivers and Global Positioning System (GPS) transceivers.

Another type of input device is a control device 416, which may perform cursor control or other automated control functions such as navigation in a graphical interface on a display screen, alternatively or in addition to input functions. Control device 416 may be a touchpad, a mouse, a trackball, or cursor direction keys for communicating direction information and command selections to processor 404 and for controlling cursor movement on display. The input device may have at least two degrees of freedom in two axes, a first axis (e.g., x) and a second axis (e.g., y), that allows the device to specify positions in a plane. Another type of input device is a wired, wireless, or optical control device such as a joystick, wand, console, steering wheel, pedal, gearshift mechanism or other type of control device. An input device 414 may include a combination of multiple different input devices, such as a video camera and a depth sensor.

In another embodiment, computer system 400 may comprise an internet of things (IoT) device in which one or more of the output device 412, input device 414, and control device 416 are omitted. Or, in such an embodiment, the input device 414 may comprise one or more cameras, motion detectors, thermometers, microphones, seismic detectors, other sensors or detectors, measurement devices or encoders and the output device 412 may comprise a special-purpose display such as a single-line LED or LCD display, one or more indicators, a display panel, a meter, a valve, a solenoid, an actuator or a servo.

When computer system 400 is a mobile computing device, input device 414 may comprise a global positioning system (GPS) receiver coupled to a GPS module that is capable of triangulating to a plurality of GPS satellites, determining and generating geo-location or position data such as latitude-longitude values for a geophysical location of the computer system 400. Output device 412 may include hardware, software, firmware and interfaces for generating position reporting packets, notifications, pulse or heartbeat signals, or other recurring data transmissions that specify a position of the computer system 400, alone or in combination with other application-specific data, directed toward host 424 or server 430.

Computer system 400 may implement the techniques described herein using customized hard-wired logic, at least one ASIC or FPGA, firmware and/or program instructions or logic which when loaded and used or executed in combination with the computer system causes or programs the computer system to operate as a special-purpose machine. According to one embodiment, the techniques herein are performed by computer system 400 in response to processor 404 executing at least one sequence of at least one instruction contained in main memory 406. Such instructions may be read into main memory 406 from another storage medium, such as storage 410. Execution of the sequences of instructions contained in main memory 406 causes processor 404 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage 410. Volatile media includes dynamic memory, such as memory 406. Common forms of storage media include, for example, a hard disk, solid state drive, flash drive, magnetic data storage medium, any optical or physical data storage medium, memory chip, or the like.

Storage media is distinct from but may be used in conjunction with transmission media. Transmission media participates in transferring information between storage media. For example, transmission media includes coaxial cables, copper wire and fiber optics, including the wires that comprise a bus of I/O subsystem 402. Transmission media can also take the form of acoustic or light waves, such as those generated during radio-wave and infra-red data communications.

Various forms of media may be involved in carrying at least one sequence of at least one instruction to processor 404 for execution. For example, the instructions may initially be carried on a magnetic disk or solid-state drive of a remote computer. The remote computer can load the instructions into its dynamic memory and send the instructions over a communication link such as a fiber optic or coaxial cable or telephone line using a modem. A modem or router local to computer system 400 can receive the data on the communication link and convert the data to a format that can be read by computer system 400. For instance, a receiver such as a radio frequency antenna or an infrared detector can receive the data carried in a wireless or optical signal and appropriate circuitry can provide the data to I/O subsystem 402 such as place the data on a bus. I/O subsystem 402 carries the data to memory 406, from which processor 404 retrieves and executes the instructions. The instructions received by memory 406 may optionally be stored on storage 410 either before or after execution by processor 404.

Computer system 400 also includes a communication interface 418 coupled to bus 402. Communication interface 418 provides a two-way data communication coupling to network link(s) 420 that are directly or indirectly connected to at least one communication networks, such as a network 422 or a public or private cloud on the Internet. For example, communication interface 418 may be an Ethernet networking interface, integrated-services digital network (ISDN) card, cable modem, satellite modem, or a modem to provide a data communication connection to a corresponding type of communications line, for example an Ethernet cable or a metal cable of any kind or a fiber-optic line or a telephone line. Network 422 broadly represents a local area network (LAN), wide-area network (WAN), campus network, internetwork, or any combination thereof. Communication interface 418 may comprise a LAN card to provide a data communication connection to a compatible LAN, or a cellular radiotelephone interface that is wired to send or receive cellular data according to cellular radiotelephone wireless networking standards, or a satellite radio interface that is wired to send or receive digital data according to satellite wireless networking standards. In any such implementation, communication interface 418 sends and receives electrical, electromagnetic, or optical signals over signal paths that carry digital data streams representing various types of information.

Network link 420 typically provides electrical, electromagnetic, or optical data communication directly or through at least one network to other data devices, using, for example, satellite, cellular, Wi-Fi, or BLUETOOTH technology. For example, network link 420 may provide a connection through a network 422 to a host computer 424.

Furthermore, network link 420 may provide a connection through network 422 or to other computing devices via internetworking devices and/or computers that are operated by an Internet Service Provider (ISP) 426. ISP 426 provides data communication services through a world-wide packet data communication network represented as internet 428. A server computer 430 may be coupled to internet 428. Server 430 broadly represents any computer, data center, virtual machine, or virtual computing instance with or without a hypervisor, or computer executing a containerized program system such as DOCKER or KUBERNETES. Server 430 may represent an electronic digital service that is implemented using more than one computer or instance and that is accessed and used by transmitting web services requests, uniform resource locator (URL) strings with parameters in HTTP payloads, API calls, app services calls, or other service calls. Computer system 400 and server 430 may form elements of a distributed computing system that includes other computers, a processing cluster, server farm or other organization of computers that cooperate to perform tasks or execute applications or services. Server 430 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. Server 430 may comprise a web application server that hosts a presentation layer, application layer and data storage layer such as a relational database system using structured query language (SQL) or no SQL, an object store, a graph database, a flat file system or other data storage.

Computer system 400 can send messages and receive data and instructions, including program code, through the network(s), network link 420 and communication interface 418. In the Internet example, a server 430 might transmit a requested code for an application program through Internet 428, ISP 426, local network 422 and communication interface 418. The received code may be executed by processor 404 as it is received, and/or stored in storage 410, or other non-volatile storage for later execution.

The execution of instructions as described in this section may implement a process in the form of an instance of a computer program that is being executed and consisting of program code and its current activity. Depending on the operating system (OS), a process may be made up of multiple threads of execution that execute instructions concurrently. In this context, a computer program is a passive collection of instructions, while a process may be the actual execution of those instructions. Several processes may be associated with the same program; for example, opening up several instances of the same program often means more than one process is being executed. Multitasking may be implemented to allow multiple processes to share processor 404. While each processor 404 or core of the processor executes a single task at a time, computer system 400 may be programmed to implement multitasking to allow each processor to switch between tasks that are being executed without having to wait for each task to finish. In an embodiment, switches may be performed when tasks perform input/output operations, when a task indicates that it can be switched, or on hardware interrupts. Time-sharing may be implemented to allow fast response for interactive user applications by rapidly performing context switches to provide the appearance of concurrent execution of multiple processes simultaneously. In an embodiment, for security and reliability, an operating system may prevent direct communication between independent processes, providing strictly mediated and controlled inter-process communication functionality.

6.0 Software Overview

Figure 5:
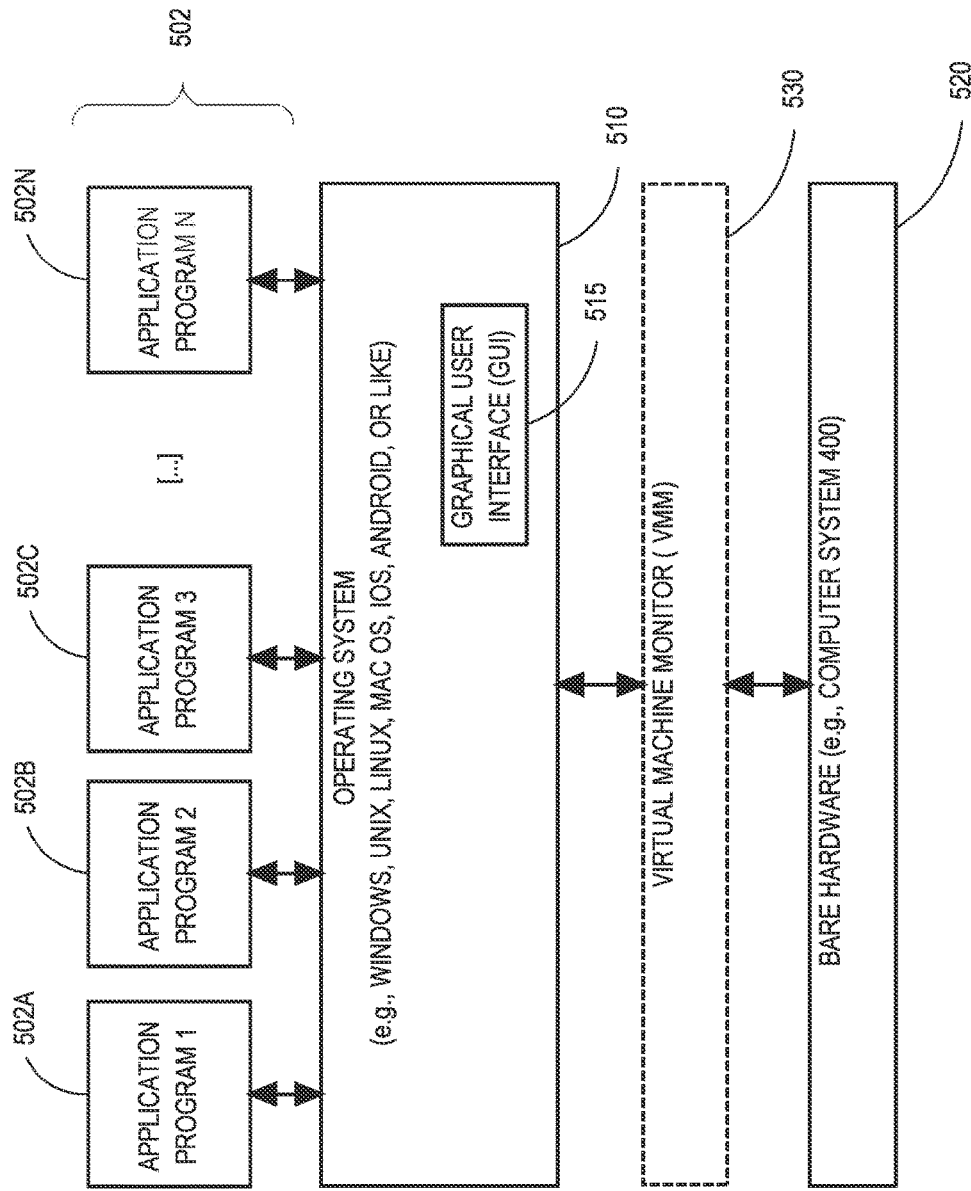
FIG. 5 illustrates a block diagram of a basic software system for controlling the operation of a computing device.

FIG. 5 is a block diagram of a basic software system 500 that may be employed for controlling the operation of computing device 400. Software system 500 and its components, including their connections, relationships, and functions, is meant to be exemplary only, and not meant to limit implementations of the example embodiment(s). Other software systems suitable for implementing the example embodiment(s) may have different components, including components with different connections, relationships, and functions.

Software system 500 is provided for directing the operation of computing device 400. Software system 500, which may be stored in system memory (RAM) 406 and on fixed storage (e.g., hard disk or flash memory) 410, includes a kernel or operating system (OS) 510.

The OS 510 manages low-level aspects of computer operation, including managing execution of processes, memory allocation, file input and output (I/O), and device I/O. One or more application programs, represented as 502A, 502B, 502C . . . 502N, may be "loaded" (e.g., transferred from fixed storage 410 into memory 406) for execution by the system 500. The applications or other software intended for use on device 500 may also be stored as a set of downloadable computer-executable instructions, for example, for downloading and installation from an Internet location (e.g., a Web server, an app store, or other online service).

Software system 500 includes a graphical user interface (GUI) 515, for receiving user commands and data in a graphical (e.g., "point-and-click" or "touch gesture") fashion. These inputs, in turn, may be acted upon by the system 500 in accordance with instructions from operating system 510 and/or application(s) 502. The GUI 515 also serves to display the results of operation from the OS 510 and application(s) 502, whereupon the user may supply additional inputs or terminate the session (e.g., log off).

OS 510 can execute directly on the bare hardware 520 (e.g., processor(s) 404) of device 400. Alternatively, a hypervisor or virtual machine monitor (VMM) 530 may be interposed between the bare hardware 520 and the OS 510. In this configuration, VMM 530 acts as a software "cushion" or virtualization layer between the OS 510 and the bare hardware 520 of the device 400.

VMM 530 instantiates and runs one or more virtual machine instances ("guest machines"). Each guest machine comprises a "guest" operating system, such as OS 510, and one or more applications, such as application(s) 502, designed to execute on the guest operating system. The VMM 530 presents the guest operating systems with a virtual operating platform and manages the execution of the guest operating systems.

In some instances, the VMM 530 may allow a guest operating system to run as if it is running on the bare hardware 520 of device 400 directly. In these instances, the same version of the guest operating system configured to execute on the bare hardware 520 directly may also execute on VMM 530 without modification or reconfiguration. In other words, VMM 530 may provide full hardware and CPU virtualization to a guest operating system in some instances.

In other instances, a guest operating system may be specially designed or configured to execute on VMM 530 for efficiency. In these instances, the guest operating system is "aware" that it executes on a virtual machine monitor. In other words, VMM 530 may provide para-virtualization to a guest operating system in some instances.

The above-described basic computer hardware and software is presented for purpose of illustrating the basic underlying computer components that may be employed for implementing the example embodiment(s). The example embodiment(s), however, are not necessarily limited to any particular computing environment or computing device configuration. Instead, the example embodiment(s) may be implemented in any type of system architecture or processing environment that one skilled in the art, in light of this disclosure, would understand as capable of supporting the features and functions of the example embodiment(s) presented herein.

7.0 Other Aspects of Disclosure

Although some of the figures described in the foregoing specification include flow diagrams with steps that are shown in an order, the steps may be performed in any order, and are not limited to the order shown in those flowcharts. Additionally, some steps may be optional, may be performed multiple times, and/or may be performed by different components. All steps, operations and functions of a flow diagram that are described herein are intended to indicate operations that are performed using programming in a special-purpose computer or general-purpose computer, in various embodiments. In other words, each flow diagram in this disclosure, in combination with the related text herein, is a guide, plan or specification of all or part of an algorithm for programming a computer to execute the functions that are described. The level of skill in the field associated with this disclosure is known to be high, and therefore the flow diagrams and related text in this disclosure have been prepared to convey information at a level of sufficiency and detail that is normally expected in the field when skilled persons communicate among themselves with respect to programs, algorithms and their implementation.

In the foregoing specification, the example embodiment(s) of the present invention have been described with reference to numerous specific details. However, the details may vary from implementation to implementation according to the requirements of the particular implement at hand. The example embodiment(s) are, accordingly, to be regarded in an illustrative rather than a restrictive sense.

What is claimed is:

1. A computer-implemented method to generate a predicted formula of a plant-based food item to mimic a target food item that is not plant-based, the method comprising:

collecting first digital data representing combinations of ingredients;

determining features of each combination of the combinations of ingredients;

generating a plurality of digitally stored feature vectors, comprising representing the features of each combination of the combinations of ingredients as a digitally stored feature vector, wherein each digitally stored feature vector represents a set of features including at least one chemical feature, nutritional feature, and molecular feature;

generating a plurality of digitally stored ingredients vectors, comprising representing each combination of the combinations of ingredients as a digitally stored ingredients vector, wherein each digitally stored ingredients vector associated with a combination of ingredients includes a proportion of each ingredient in the combination of ingredients;

creating a training set for use in training a neural network, the training set comprising the plurality of digitally stored feature vectors and the plurality of digitally stored ingredients vectors associated with the combinations of ingredients;

training, using the training set, the neural network in a first stage to match the plurality of digitally stored feature vectors and the plurality of digitally stored ingredients vectors by modifying parameters of the neural network;

identifying features of the target food item and, in response, representing the features of the target food item as a digitally stored feature vector; and applying the trained neural network to the digitally stored feature vector of the target food item in a second stage to generate the predicted formula that includes a set of ingredients and a respective proportion of each ingredient in the set of ingredients.

2. The method of claim 1, wherein the combinations of ingredients include true combinations of ingredients, wherein the true combinations of ingredients are from recipes in a recipes database.

3. The method of claim 1, wherein the combinations of ingredients include synthetic combinations of ingredients, wherein each synthetic combination of ingredients of the synthetic combinations of ingredients includes ingredients randomly selected from an ingredients database.

4. The method of claim 1, wherein each digitally stored feature vector of the plurality of digitally stored feature vectors is matched with a digitally stored ingredients vector from the plurality of digitally stored ingredients vectors in the first stage.

5. The method of claim 1, wherein each digitally stored ingredients vector of the plurality of digitally stored ingredients vectors is matched with a digitally stored feature vector from the plurality of digitally stored feature vectors in the first stage.

6. The method of claim 1, wherein the trained neural network is applied in reverse in the second stage to generate the predicted formula.

7. The method of claim 1, further comprising refining the predicted formula to reduce a total number of ingredients in the set of ingredients and to rebalance proportions of remaining ingredients in the set of ingredients.

8. The method of claim 1, wherein the plant-based food item is prepared by using the predicted formula.

9. The method of claim 1, wherein the neural network comprises N hidden layers, wherein N is an integer greater than one.

10. The method of claim 9, wherein the N hidden layers include a first hidden layer and one or more subsequent hidden layers after the first hidden layer, wherein a size of each subsequent hidden layer is either double or half a size of its previous layer.

11. One or more non-transitory computer-readable storage media storing one or more instructions programmed for generating a predicted formula of a plant-based food item to mimic a target food item that is not plant-based and which, when executed by one or more computing devices, cause:

collecting first digital data representing combinations of ingredients;

determining features of each combination of the combinations of ingredients;

generating a plurality of digitally stored feature vectors, comprising representing the features of each combination of the combinations of ingredients as a digitally stored feature vector, wherein each digitally stored feature vector represents a set of features including at least one chemical feature, nutritional feature, and molecular feature;

generating a plurality of digitally stored ingredients vectors, comprising representing each combination of the combinations of ingredients as a digitally stored ingredients vector, wherein each digitally stored ingredients vector associated with a combination of ingredients includes a proportion of each ingredient in the combination of ingredients;

creating a training set for use in training a neural network, the training set comprising the plurality of digitally stored feature vectors and the plurality of digitally stored ingredients vectors associated with the combinations of ingredients;

training, using the training set, the neural network in a first stage to match the plurality of digitally stored feature vectors and the plurality of digitally stored ingredients vectors by modifying parameters of the neural network;

identifying features of the target food item and, in response, representing the features of the target food item as a digitally stored feature vector; and applying the trained neural network to the digitally stored feature vector of the target food item in a second stage to generate the predicted formula that includes a set of ingredients and a respective proportion of each ingredient in the set of ingredients.

12. The one or more non-transitory computer-readable storage media of claim 11, wherein the combinations of ingredients include true combinations of ingredients, wherein the true combinations of ingredients are from recipes in a recipes database.

13. The one or more non-transitory computer-readable storage media of claim 11, wherein the combinations of ingredients include synthetic combinations of ingredients, wherein each synthetic combination of ingredients of the synthetic combinations of ingredients includes ingredients randomly selected from an ingredients database.

14. The one or more non-transitory computer-readable storage media of claim 11, wherein each digitally stored feature vector of the plurality of digitally stored feature vectors is matched with a digitally stored ingredients vector from the plurality of digitally stored ingredients vectors in the first stage.

15. The one or more non-transitory computer-readable storage media of claim 11, wherein each digitally stored ingredients vector of the plurality of digitally stored ingredients vectors is matched with a plurality of digitally stored feature vector from the plurality of digitally stored feature vectors in the first stage.

16. The one or more non-transitory computer-readable storage media of claim 11, wherein the trained neural network is applied in reverse in the second stage to generate the predicted formula.

17. The one or more non-transitory computer-readable storage media of claim 11, wherein the one or more instructions, when executed by the one or more computing devices, further cause, refining the predicted formula to reduce a total number of ingredients in the set of ingredients and to rebalance proportions of remaining ingredients in the set of ingredients.

18. The one or more non-transitory computer-readable storage media of claim 11, wherein the plant-based food item is prepared by using the predicted formula.

19. The one or more non-transitory computer-readable storage media of claim 11, wherein the neural network comprises N hidden layers, wherein N is an integer greater than one.

20. The one or more non-transitory computer-readable storage media of claim 19, wherein the N hidden layers include a first hidden layer and one or more subsequent hidden layers after the first hidden layer, wherein a size of each subsequent hidden layer is either double or half a size of its previous layer.

* * * * *

UNITED STATES PATENT AND TRADEMARK OFFICE
CERTIFICATE OF CORRECTION

PATENT NO. : 10,957,424 B1
APPLICATION NO. : 16/989413
DATED : March 23, 2021
INVENTOR(S) : Yoan Navon et al.

Page 1 of 1

It is certified that error appears in the above-identified patent and that said Letters Patent is hereby corrected as shown below:

In the Claims

Column 20, Line 54, Claim 15, delete "plurality of" after "matched with a".

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*